United States Patent [19]

Lavielle et al.

[11] Patent Number: 4,820,707
[45] Date of Patent: Apr. 11, 1989

[54] 2,6-PIPERAZINEDIONE COMPOUNDS

[75] Inventors: Gilbert Lavielle, La Celle Saint Cloud; Jean C. Poignant, Bures sur Yvette, both of France

[73] Assignee: ADIR Et Cie, Neuilly-sur-Seine, France

[21] Appl. No.: 70,967

[22] Filed: Jul. 8, 1987

[30] Foreign Application Priority Data

Jul. 9, 1986 [FR] France ................. 86 09977

[51] Int. Cl.$^4$ ................. A61K 31/495; C07D 401/14; C07D 403/08
[52] U.S. Cl. ................. 514/252; 544/357; 544/360; 544/392
[58] Field of Search .......... 514/252; 544/357

[56] References Cited

U.S. PATENT DOCUMENTS

| | | | |
|---|---|---|---|
| 4,275,063 | 6/1981 | Creighton | 514/252 |
| 4,748,240 | 5/1988 | Stack | 544/357 |
| 4,757,073 | 7/1988 | New | 514/252 |

FOREIGN PATENT DOCUMENTS

| | | | |
|---|---|---|---|
| 230474 | 8/1987 | European Pat. Off. | 544/357 |
| 2326923 | 6/1977 | France | 514/252 |

OTHER PUBLICATIONS

Cai, J. C., Chem. Abstract 106:176424n–abstract of WO 87/00,170 (1/15/87).

*Primary Examiner*—Donald G. Daus
*Assistant Examiner*—Mark W. Noel
*Attorney, Agent, or Firm*—Gordon W. Hueschen

[57] ABSTRACT

The invention relates to 2,6-piperazinedione derivatives of general formula I

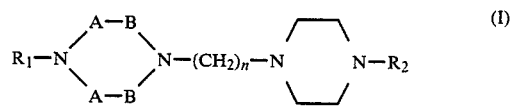

in which:
A and B each denote a methylene radical or a carbonyl radical with the proviso, however, that A and B never simultaneously denote the same radical, $R_1$ denotes a diphenylmethyl radical optionally substituted on the benzene rings with a halogen atom, a cyclohexyl radical, a pyridylmethyl group, or a benzyl radical optionally substituted with a halogen atom or with an alkoxy radical containing from 1 to 4 carbon atoms, $R_2$ denotes a pyrimidinyl radical or a phenyl radical optionally substituted with a halogen atom, with an alkyl radical having from 1 to 4 carbon atoms, with a trifluoromethyl radical or with an alkoxy radical containing from 1 to 4 carbon atoms, n is an integer from 2 to 4, and their addition salts with a pharmaceutically acceptable inorganic or organic acid.

14 Claims, No Drawings

2,6-PIPERAZINEDIONE COMPOUNDS

The present invention relates to new 2,6-piperazinedione compounds, to the processes for preparing them and to the pharmaceutical compositions containing them.

Certain 2,6-piperazinedione compounds having sedative effects on the central nervous system are known (De Jong D. et al. J. Pharm. 1959, 11, p. 393-399).

The new 2,6-piperazinedione compounds possess very advantageous pharmacological properties, and in particular very powerful anxiolytic, antiaggression and antipsychotic properties. On the other hand, they are devoid of the side effects traditionally encountered in this pharmacological class. In effect, the compounds of the present invention do not have sedative, anticonvulsant or muscle-relaxant effects, and differ in this respect from other, already known 2,6-piperazinedione compounds. On the other hand, the compounds of the invention are clearly distinguished by their chemical structure from the other piperazines already described.

The subject of the present invention is more especially the 2,6-piperazinedione compounds of general formula I:

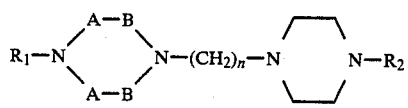   (I)

in which:
- A and B each denote a methylene radical or a carbonyl radical with the proviso, however, that A and B never simultaneously denote the same radical,
- $R_1$ denotes a diphenylmethyl radical optionally substituted on the benzene rings with a halogen atom, a cycohexyl radical, a pyridylmethyl group, or a benzyl radical optionally substituted with a halogen atom or with an alkoxy radical containing from 1 to 4 carbon atoms,
- $R_2$ denotes a pyrimidinyl radical or a phenyl radical optionally substituted with a halogen atom, with an alkyl radical having from 1 to 4 carbon atoms, with a trifluoromethyl radical or with an alkoxy radical containing from 1 to 4 carbon atoms,
- n is an integer which can assume values from 2 to 4, and their salts formed by addition to a pharmaceutically acceptable inorganic or organic acid.

The subject of the present invention is also the process for preparing compounds of general formula I, wherein:
either an imide of general formula II:

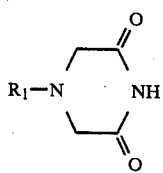   (II)

in which the definition of the substituent $R_1$ remains that mentioned above, is condensed with a compound of general formula III:

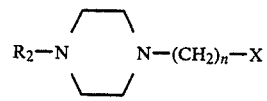   (III)

in which $R_2$ is as defined above, n is an integer equal to 2 or 3 and X denotes a chlorine or bromine atom, to obtain the compounds of formula I in which the definition of $R_1$ and $R_2$ remains that stated above, n is an integer equal to 2 or 3, A denotes a methylene and B a carbonyl, or the compound of general formula II is reacted with 1-bromo-3-chloropropane in the presence of a metal hydride to obtain a compound of general formula IV:

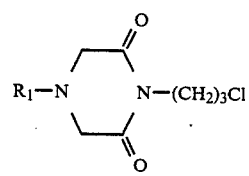   (IV)

in which $R_1$ has the meaning defined above for the formula I, and the 1-(3-chloropropyl)-2,6-piperazinedione thereby obtained is then condensed with a piperazine of general formula V:

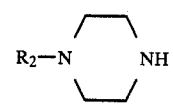   (V)

in which the definition of $R_2$ remains that stated above, to obtain a compound of general formula I in which $R_1$ and $R_2$ have the meanings defined above, n equals 3, A denotes a methylene and B a carbonyl, or:

a 2,6-morpholinedione of general formula VI

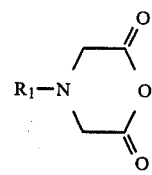   (VI)

in which $R_1$ has the meaning defined above for the formula I, is condensed with a 4-piperazinylbutylamine of general formula VII:

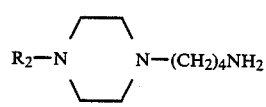   (VII)

in which the definition of $R_2$ remains identical to that given for the formula I, to obtain a compound of formula I in which the definition of $R_1$ and $R_2$ remains that stated above, n equals 4, A denotes a methylene and B a carbonyl, or:

a piperazinedione of general formula VIII:

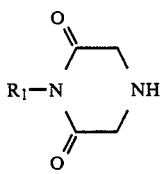

(VIII)

in which $R_1$ has the meaning defined above for the formula I, is condensed wtih a piperazine compound of general formula III, to obtain a compound of general formula I in which $R_1$, $R_2$ and n have the meanings defined above, A denotes a carbonyl and B denotes a methylene.

The compounds of general formula I may then be converted, if so desired, to their addition salts with a pharmaceutically acceptable inorganic or organic acid.

The imides of general formula II are obtained by heating the corresponding diacids in the presence of formamide. These acids are prepared by the action of 2-chloroacetic acid on the corresponding primary amines (Organic Syntheses Collective Vol. II, John Wiley and Sons Ed. N.Y., 1943, p. 397). They can also be synthesized by alkylation of 2,6-piperazinedione with an alkyl halide (Bull. Soc. Chim. France, 1968, 8, 3248).

The compounds of general formula III are obtained, in the case where n equals 2, by condensation of ethylene oxide with the corresponding piperazine (J.A.C.S. 1948, 70, p. 2015), followed by chlorination of the alcohol obtained using thionyl chloride. In the case of n equals 3, the compounds of general formula III are obtained by the action of 1-bromo-3-chloropropane on the corresponding piperazine (Bull. Soc. Chim. France, 1968, 8, p. 3247).

The synthesis of the 2,6-morpholinediones of general formula VI is known (Organic Syntheses Collective Vol. I, John Wiley and Sons Ed. N.Y. 1943, p. 91).

The 4-piperazinylbutylamines of general formula VII are obtained by reduction of the corresponding nitriles in the presence of metal hydrides such as lithium aluminum double hydride (J. Med. Chem., 1972, 15, 5, p. 477).

The preparation of these nitriles is known (Bull. Soc. Chim. France, 1968, 8, 3247).

The compounds of the general formula VIII are prepared by condensation of 4-benzyl-2,6-piperazinedione with the corresponding alkyl halides, followed by a debenzylation by hydrogenolysis.

Condensation of the imides of general formula II with the compounds of general formula III is preferably performed in a polar anhydrous organic solvent such as dimethylformamide in the presence of a metal hydride such as sodium hydride and an inorganic salt such as sodium iodide, and at a temperature of between 40° C. and 100° C.

The condensation of the 2,6-piperazinediones of general formula IV with piperazines of general formula V, and that of the piperazinediones of general formula VIII with the compounds of general formula III, are carried out in a polar organic solvent such as 2-butanone in the presence of inorganic salts such as sodium carbonate and sodium iodide, at a temperature of between 40° and 100° C.

The reaction of the 2,6-morpholinediones of general formula VI with the 4-piperazinylbutylamines of general formula VII is performed in a basic organic solvent such as pyridine at a temperature of between 40° C. and 100° C.

Among the pharmaceutically acceptable acids for the preparation of the addition salts with the compounds of general formula I, there may be mentioned phosphoric, hydrochloric, citric, oxalic, sulfuric, tartaric, mandelic, trimethanesulfonic acids, and the like.

The compounds according to the invention, as well as their salts, are endowed with highly advantageous pharmacological properties.

In effect, the pharmacological trials in vivo showed that these compounds possess anxiolytic, antiaggression and antipsychotic properties. These properties were demonstrated by means of traditionally used trials in animals, enabling the anxiolytic, antiaggression or antipsychotic activity of the new compounds in man to be predicted with a very high degree of accuracy (Dallas Treit, Neur. Biob. Rev., 1985, 9, p. 203–222).

On the other hand, the compounds of the present invention are devoid of sedative properties in respect of the central nervous system, and differ from other, already known, 2,6-piperazinedione compounds.

The compounds of the present invention show, in particular, a profile corresponding to an anxio-selective psychotropic agent. Their pharmacological properties enable them to be applied in the treatment of anxiety in all its forms.

The invention also extends to the pharmaceutical compositions containing, as active principle, at least one compound of general formula I or one of its addition salts with a pharmaceutically compatible inorganic or organic acid, in combination with one or more inert and suitable excipients.

The pharmaceutical compositions thereby obtained are advantageously presented in various forms, such as, for example, tablets, dragees, gelatin capsules, sublingual tablets or other galenical preparations suitable for sublingual administration, suppositories, or solutions for injection or to be taken by mouth.

The dosage can vary widely according to the age and weight of the patient, and the nature and severity of the condition, as well as the administration route.

The preferred administration route is the oral or parenteral route. In general, the unit dosage will range between 0.1 and 100 mg, and the daily dosage which may be used in human therapy between 0.1 and 300 mg.

The examples which follow, which are given without implied limitation, illustrate the invention.

The stated melting points are measured according to the micro-Köfler technique. The infrared spectra are obtained with solutions of the products in Nujol. The proton nuclear magnetic resonance (NMR) spectra were recorded at 60 MHz.

EXAMPLE 1

4-(2-Fluorobenzyl)-1-{3-[1-(3-trifluoromethylphenyl)-4-piperazinyl]propyl}-2,6-piperazinedione dimandelate

STAGE A 1-(3-Chloropropyl)-4-(2-fluorobenzyl)-2,6-piperazinedione

A suspension is prepared of 0.12 mole of sodium hydride in 100 ml of dimethylformamide. 0.12 mole of 4-(2-fluorobenzyl)-2,6-piperazinedione dissolved in 50 ml of dimethylformamide is added. The mixture is heated to 70° C. for 30 min. The mixture is cooled and 0.13 mole of 1-bromo-3-chloropropane added. The mixture is left to react at room temperature until the imide has completely disappeared. The organic solvent is then removed under vacuum and the residue taken up with 100 ml of water and 200 ml of benzene.

The mixture is decanted, the aqueous phase removed and the organic phase evaporated. The residue is ground in ether. Pure crystals of 1-(3-chloropropyl)-4-(2-fluorobenzyl)-2,6-piperazinedione are obtained.

Yield: 96%.

STAGE B

A mixture containing 6 g of sodium carbonate and 0.5 g of sodium iodide is added to a solution of 0.025 mole of 1-(3-chloropropyl)-4-(2-fluorobenzyl)-2,6-piperazinedione obtained above and 0.0275 mole of 1-(3-trifluoromethylphenyl)piperazine in 200 ml of 2-butanone. The mixture is brought to reflux for 40 hours and then filtered and concentrated under vacuum. The residue is taken up in benzene and the benzene phase washed three times with distilled water. The organic phase is dried over anhydrous sodium sulfate and the solvent evaporated off. The residue obtained is purified by chromatography on a silica column, using a mixture of dichloromethane and methanol (95:5) as eluant. The eluant is evaporated off and the residue dissolved in the minimum of acetone. 0.028 mole of mandelic acid is added with stirring. 4-(2-Fluorobenzyl)-1-{3-8 1-(3-trifluoromethylphenyl)-4-piperazinyl]propyl}-2,6-piperazinedione dimandelate is precipitated by adding a mixture of isopropyl ether and hexane (50:50).

Yield: 54%; Melting point: 82° C. The spectral physical constants of the base are shown in Table I.

EXAMPLES 2-4

The following compounds were prepared according to the process described in Example 1. Their spectral physical structures are shown in Table I.

EXAMPLE 2

4-(2-Fluorobenzyl)-1-{3-8 1-(3-chlorophenyl)-4-piperazinyl]propyl}-2,6-piperazinedione dimandelate Yield 60%; Melting point: 50° C.

EXAMPLE 3

4-(2-Chlorobenzyl)-1-{3-8 1-(3-chlorophenyl)-4-piperazinyl]propyl}-2,6-piperazinedione dimandelate
Yield: 44%; Melting point: 75° C.

EXAMPLE 4

4-(2-Chlorobenzyl)-1-{3-[1-(3-trifluoromethylphenyl)-4-piperazinyl]propyl}-2,6-piperazinedione dimandelate Yield: 68%; Melting point: 92° C.

EXAMPLE 5

4-Benzyl-1-{4-[1-(2-pyrimidinyl)-4-piperazinyl]butyl}-2,6-piperazinedione trihydrochloride 0.066 mole of N-benzyl-2,6-morpholinedione and 0.066 mole of 4-(2-pyrimidinyl)-1-(4-aminobutyl)piperazine dissolved in 200 ml of pyridine are heated to reflux for 12 hours.

The organic solvent is then evaporated off under vacuum and the residue obtained chromatographed on 500 g of finely disperse silica, using a mixture of dichloromethane and methanol (95:5) as eluant. The eluant is evaporated off under vacuum and the residue obtained dissolved in the minimum of acetone. 12.6 ml of 5.28N ethanolic hydrogen chloride are added with stirring and the precipitated salt is isolated by filtration.

Yield: 35%; Melting point: 175° C.

The spectral physical constants of 4-benzyl-1-{4-[1-(2-pyrimidinyl)-4-piperazinyl]butyl}-2,6-piperazinedione trihydrochloride are shown in Table I.

EXAMPLE 6

4-(2-Methoxybenzyl)-1-{4-[1-(3-trifluoromethylphenyl)-4-piperazinyl]butyl}-2,6-piperazinedione dihydrochloride 0.022 mole of 4-(2-methoxybenzyl)-2,6-morpholinedione and 0.022 mole of 4-(3-trifluoromethylbenzyl)-1-(4-aminobutyl)piperazine in 80 ml of pyridine are heated to reflux for 40 hours. The reaction medium is then concentrated under vacuum and washed with saturated sodium carbonate solution. The mixture is extracted with chloroform and dried over anhydrous sodium sulfate, and the chloroform phase is evaporated under vacuum. The residue is chromatographed on a column containing 350 g of finely disperse silica, using a mixture of dichloromethane and methanol (95:5) as eluant. The eluate is recovered, the eluant evaporated off under vacuum and the residue dissolved in ethyl ether containing acetone. 8.3 ml of 5.28N ethanolic hydrogen chloride are added to this solution with stirring, and the salt formed is isolated by filtration.

Yield: 64%; Melting point: 120° C.

The spectral physical constants of the corresponding base are shown in Table I.

EXAMPLE 7

4-(2-Pyridylmethyl)-1-{3-[1-(4-fluorophenyl)-4-piperazinyl]propyl}-2,6-piperazinedione trihydrochloride A suspension of 0.098 mole of sodium hydride in 30 ml of anhydrous dimethylformamide is heated to 60° C. A solution of 0.098 mole of 4-(2-pyridylmethyl)-2,6-piperazinedione in 15 ml of anhydrous dimethylformamide is added dropwise. When the addition is complete, the mixture is maintained at 60° C. for two hours. The reaction medium is then cooled to 25° C. and a solution of 0.126 mole of 4-(4-fluorophenyl)-1-(3-chloropropyl)piperazine in 10 ml of anhydrous dimethylformamide and 0.1 g of sodium iodide are added rapidly. The mixture is heated to 70° C. until the starting 2,6-piperazinedione has completely disappeared. The reaction medium is concentrated under vacuum. The solid residue is recrystallized in a mixture of iospropyl ether and ethanol (90:10). Pure crystals of 4-(2-pyridylmethyl)-1-{3-[1-(4-fluorophenyl)-4-piperazinyl]propyl}-2,6-piperazinedione are obtained.

Yield: 60%; Melting point: 90° C.

11.2 ml of 5.28N ethanolic hydrogen chloride are added with stirring to 0.0588 mole of the base obtained above. The crystals of 4-(2-pyridylmethyl)-1-{3-[1-(4-fluorophenyl)-4-piperazinyl]propyl}-2,6-piperazinedione trihydrochloride are isolated by filtration.

Melting point: 120° C.

The spectral physical constants of 4-(2-pyridylmethyl)-1-{3-[1-(4-fluorophenyl)-4-piperazinyl]-propyl}-2,6-piperazinedione trihydrochloride are shown in Table I.

The following compounds were prepared according to the process described in Example 7. Their spectral physical constants are shown in Table I.

EXAMPLE 8

4-Benzyl-1-{3-[1-(3-chlorophenyl)-4-piperazinyl]-propyl}-2,6-piperazinedione hydrochloride Yield: 39%; Melting point: 197° C.

EXAMPLE 9

4-Benzyl-1-{3-[1-(4-fluorophenyl)-4-piperazinyl]-propyl}-2,6-piperazinedione oxalate Yield: 45%; Melting point: 190° C.

EXAMPLE 10

4-Benzyl-1-{2-[1-(3-trifluoromethylphenyl)-4-piperazinyl]ethyl}-2,6-piperazinedione dihydrochloride Yield: 38%; Melting point: 196° C.

EXAMPLE 11

4-(2-Methoxybenzyl)-1-{3-[1-(3-chlorophenyl)-4-piperazinyl]propyl}-2,6-piperazinedione dihydrochloride Yield: 50%; Melting point: 150° C.

EXAMPLE 12

4-(2-Methoxybenzyl)-1-{3-[1-(4-fluorophenyl)-4-piperazinyl]propyl}-2,6-piperazinedione dihydrochloride Yield: 20%; Melting point: 220° C.

EXAMPLE 13

4-(2-Methoxybenzyl)-1-{3-[1-(2-methylphenyl)-4-piperazinyl]propyl}-2,6-piperazinedione oxalate Yield: 47%; Melting point: 203° C.

EXAMPLE 14

4-(2-Methoxybenzyl)-1-{3-[1-(4-methylphenyl)-4-piperazinyl]propyl}-2,6-piperazinedione Yield: 35%; Melting point: 123° C.

EXAMPLE 15

4-(2-Methoxybenzyl)-1-{3-[1-(3-trifluoromethyl-phenyl)-4-piperazinyl]propyl}-2,6-piperazinedione dihydrochloride Yield: 80%; Melting point: 130°–140° C.

EXAMPLE 16

4-(2-Methoxybenzyl)-1-{2-[1-(3-trifluoromethyl-phenyl)-4-piperazinyl]ethyl}-2,6-piperazinedione trihydrochloride Yield: 65%; Melting point: 158° C.

EXAMPLE 17

4-(2-Pyridylmethyl)-1-{3-[1-(2-chlorophenyl)-4-piperazinyl]propyl}-2,6-piperazinedione trihydrochloride Yield: 56%; Melting point: 160° C.

EXAMPLE 18

4-(2-Pyridylmethyl)-1-{3-[1-(2-methoxyphenyl)-4-piperazinyl]propyl}-2,6-piperazinedione tetrahydrochloride Yield: 42%; Melting point: 185° C.

EXAMPLE 19

4-(2-Pyridylmethyl)-1-{3-[1-(2-methylphenyl)-4-piperazinyl]propyl}-2,6-piperazinedione trihydrochloride Yield: 48%; Melting point: 190° C.

EXAMPLE 20

4-(2-Pyridylmethyl)-1-{3-[1-(4-methylphenyl)-4-piperazinyl]propyl}-2,6-piperazinedione trihydrochloride Yield: 51%; Melting point: 203° C.

EXAMPLE 21

4-(2-Pyridylmethyl)-1-{3-[1-(3-trifluoromethylphenyl)-4-piperazinyl]propyl}-2,6-piperazinedione dioxalate Yield: 55%; Melting point: 152° C.

EXAMPLE 22

4-(3-Pyridylmethyl)-1-{3-[1-(3-chlorophenyl)-4-piperazinyl]propyl}-2,6-piperazinedione trihydrochloride Yield: 45%; Melting point: 130° C.

EXAMPLE 23

4-Diphenylmethyl-1-{3-[1-(2-methylphenyl)-4-piperazinyl]propyl}-2,6-piperazinedione trimethanesulfonate Yield: 54%; Melting point: 80° C.

EXAMPLE 24

4-Diphenylmethyl-1-{3-[1-(3-trifluoromethylphenyl)-4-piperazinyl]propyl}-2,6-piperazinedione dimandelate Yield: 48%; Melting point: 60° C.

EXAMPLE 25

4-(4-Chlorodiphenylmethyl)-1-{3-[1-(4-fluorophenyl)-4-piperazinyl]propyl}-2,6-piperazinedione dimandelate Yield: 80%; Melting point: 105° C.

EXAMPLE 26

4-(4-Chlorodiphenylmethyl)-1-{3-[1-(3-trifluoromethyl-phenyl)-4-piperazinyl]propyl}-2,6-piperazinedione dicitrate Yield: 70%; Melting point: 80° C.

EXAMPLE 27

4-Cyclohexyl-1-{3-[1-(3-trilfuoromethylphenyl)-4-piperazinyl]propyl}-2,6-piperazinedione dihydrochloride Yield: 47%; Melting point: 238° C.

EXAMPLE 28

1-Benzyl-4-{3-[1-(3-trifluoromethylphenyl)-4-piperazinyl]propyl}-2,6-piperazinedione diphosphate A mixture of 6 g of sodium carbonate and 0.4 g of sodium iodide is added to a solution of 0.0166 mole of 1-benzyl-2,6-piperazinedione and 0.019 mole of 4-(3-trifluoromethylphenyl)-3-(3-chloropropyl)piperazine in 100 ml of 2-butanone. The mixture is brought to reflux until the starting piperazinedione has completely disappeared. The medium is cooled to room temperature, the inorganic salts are filtered off and the solvent is evaporated off under vacuum. The residue is taken up in dichloromethane and washed with aqueous sodium carbonate solution and then water, and the organic phase is dried over anhydrous sodium sulfate. The solvent is evaporated off under vacuum and the residue purified by chromatography on a column of finely disperse silica (200 g) eluting with a mixture of ethyl ether and acetone (95:5). The eluant is evaporated off and the 5 g of pure product thereby obtained are dissolved in 21 ml of an M solution of phosphoric acid in acetone.

The diphosphate formed is isolated by filtration and recrystallized in 140 ml of ethanol to obtain 3.5 g of crystallized product.

Yield: 31%; Melting point: 186° C.

The spectral physical constants of 1-benzyl-4-{3-[1-(3-trifluoromethylphenyl)-4-piperazinyl]propyl}-2,6-piperazinedione diphosphate are shown in Table I.

EXAMPLE 29
1-(3-Methoxybenzyl)-4-{3-[1-(3-trifluoromethylphenyl)-4-piperazinyl]propyl}-2,6-piperazinedione diphosphate This compound was prepared according to the method described in Example 28.

Yield: 31%; Melting point: 190° C.

Its spectral physical constants are shown in Table I.

EXAMPLE 30
4-(2-Fluorobenzyl)-1-{3-[1-(5-trifluoromethyl-2-pyridinyl)-4-piperazinyl]propyl}-2,6-piperazinedione dihydrochloride This compound was prepared according to the method described in Example 1.

Melting point: 140° C.

The spectral physical constants of the corresponding base are shown in Table I.

COMPOUNDS OF GENERAL FORMULA I

| EX. | R$_1$ | A | B | n | R$_2$ | IR cm$^{-1}$ $\nu$(C=O) | NMR (solvent) (b) = base (a) = acid |
|---|---|---|---|---|---|---|---|
| 1 | 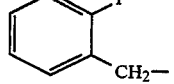 | —CH$_2$— |  | 3 | 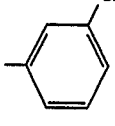 | 1680 1735 | (CDCl$_3$) (b) 1.5 to 2 ppm, m, 2H; 2.3 to 2.8 ppm, m, 6H; 3 to 3.5 ppm, m, 4H; 3.45 ppm, s, 4H; 3.75 ppm, s, 2H; 3.85 ppm, t, 2H; 6.8 to 7.6 ppm, m, 8H |
| 2 | 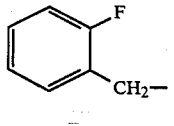 | —CH$_2$— |  | 3 | 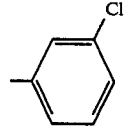 | 1680 1735 | (CDCl$_3$) (b) 1.5 to 2 ppm, m, 2.4 to 2.8 ppm, m, 6H; 3 to 3.4 ppm, m, 4H; 3.4 ppm, s, 4H; 3.7 ppm, s, 2H; 3.8 ppm, t, 2H; 6.6 to 7.6 ppm, m, 8H |
| 3 | 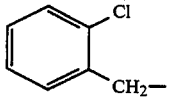 | —CH$_2$— |  | 3 | 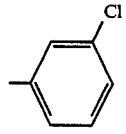 | 1685 1735 | (CDCl$_3$) (b) 1,5 to 2 ppm, m, 2H; 2.2 to 2.8 ppm, m, 6H; 3 to 3.4 ppm, m, 4H; 3.45 ppm, s, 4H; 3.7, ppm, s, 2H; 3.8 to 4 ppm, m, 2H; 6.5 to 7.5 ppm, m, 8H |
| 4 | 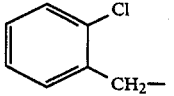 | —CH$_2$— |  | 3 | 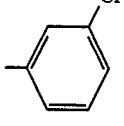 | 1680 1735 | (CDCl$_3$) (b) 1.5 to 2 ppm, m, 2.2 to 2.7 ppm, m, 6H; 3 to 3.4 ppm, m, 4H; 3.4 ppm, s, 4H; 3.7 ppm, s, 2H; 3.8 ppm, t, 2H; 6.8 to 7.6 ppm, m, 8H |
| 5 | 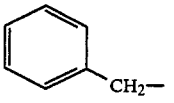 | —CH$_2$— |  | 4 | 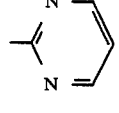 | 1690 1750 | (D$_2$O) (a) 1.3 to 1.9 ppm, m, 4H; 3.1 to 4 ppm, m, 10H; 4.1 ppm, s, 4H; 4.3 ppm, s, 2H; 4.75 ppm, s, 2H; 7.1 ppm, t, 1H; 7.6 ppm, s, 5H; 8.7 ppm, d, 2H; |
| 6 | 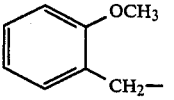 | —CH$_2$— |  | 4 | 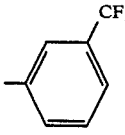 | 1675 1730 | (CDCl$_3$) (b) 1.2 to 2 ppm, m, 4H; 2.2 to 2.9 ppm, m, 6H; 3.1 to 3.5 ppm, m, 6H; 3.5 ppm, s, 4H; 3.8 ppm, s, 2H; 3.9 ppm, s, 3H; 6.8 to 7.7 ppm, m, 8H |
| 7 | 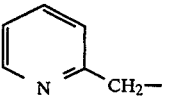 | —CH$_2$— |  | 3 |  | 1680 1730 | (D$_2$O) (a) 1.5 to 2.5 ppm, m, 2H; 3 to 4.2 ppm, m, 16H; 4.3 ppm, s, 2H; 7.2 to 7.4 ppm m, 4H; 7.9 to 9 ppm, m, 4H |

-continued

COMPOUNDS OF GENERAL FORMULA I

| EX. | R₁ | A | B | n | R₂ | IR cm⁻¹ $\nu_{(C=O)}$ | NMR (solvent) (b) = base (a) = acid |
|---|---|---|---|---|---|---|---|
| 8 | 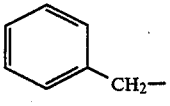 | —CH₂— | 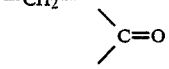 C=O | 3 |  Cl | 1680 1730 | (DMSO—d₆) (a) 1.5 to 2.3 ppm, m, 2H; 2.8 to 4.2 ppm, m, 18H; 6.7 to 7.6 ppm, m, 9H; exchangeable 1H |
| 9 | 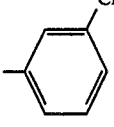 | —CH₂— | 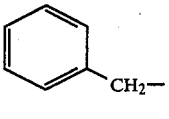 C=O | 3 |  F | 1690 1740 | (DMSO—d₆) (a) 1.6 to 2.2 ppm, m, 2H; 2.7 to 4, ppm, m, 18H; 6.9 to 7.5 ppm, m, 9H; exchangeable 2H |
| 10 |  | —CH₂— | 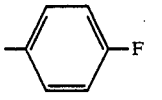 C=O | 2 | 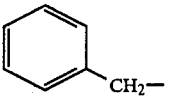 CF₃ | 1670 1730 | (CDCl₃) (b) 2.4 to 2.9 ppm, m, 6H; 3 to 3.4 ppm, m, 4H; 3.4 ppm, s, 4H; 3.65 ppm, s, 2H; 3.95 ppm, t, 2H; 6.9 to 7.5 ppm, m, 9H |
| 11 | 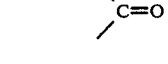 OCH₃ | —CH₂— |  C=O | 3 | 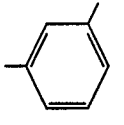 Cl | 1690 1745 | (D₂O) (a) 1.7 to 2.3 ppm, m, 2H; 3 to 4 ppm, m, 12H; 3.9 ppm, s, 3H; 4.35 ppm, s, 4H; 4.55 ppm, s, 2H; 6.8 to 7.7 ppm, m, 8H |
| 12 | 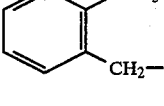 OCH₃ | —CH₂— | 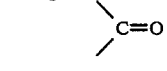 C=O | 3 |  F | 1690 1750 | (DMSO—d₆) (a) 1.7 to 2.4 ppm, m, 2H; 2.9 to 4 ppm, m, 12H; 3.9 ppm, s, 3H; 4.2 ppm, s, 4H; 4.5 ppm, s, 2H; 6.9 to 7.8 ppm, m, 8H; exchangeable 2H |
| 13 | 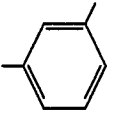 OCH₃ | —CH₂— | 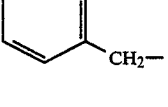 C=O | 3 | 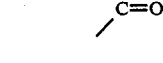 CH₃ | 1600 1740 | (DMSO—d₆) (a) 1.6 to 2.2 ppm, m, 2H; 2.3 ppm, s, 3H; 2.7 to 3.8 ppm, m, 18H; 3.8 ppm, s, 3H; 6.8 to 7.5 ppm, m, 8H; exchangeable 2H |
| 14 |  OCH₃ | —CH₂— | 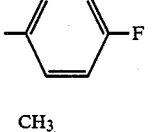 C=O | 3 | 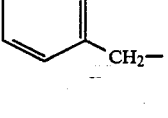 CH₃ | 1680 1730 | (CDCl₃) (b) 1.5 to 2 ppm, m, 2H; 2.25 ppm, s, 3H; 2.3 to 2.7 ppm, m, 6H; 2.9 to 3.2 ppm, m, 6H; 3.7 ppm, s, 2H; 3.4 ppm, s, 4H; 3.8 ppm, s, 3H; 6.7 to 7.4 ppm, m, 8H |
| 15 | 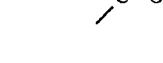 OCH₃ | —CH₂— |  C=O | 3 | 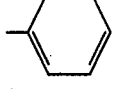 CF₃ | 1680 1735 | (CDCl₃) (b) 1.5 to 2 ppm, m, 2H; 2.2 to 2.9 ppm, m, 6H; 3 to 4 ppm, m, 15H; 6.7 to 7.6 ppm, m, 8H |
| 16 | 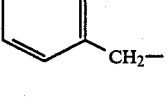 OCH₃ | —CH₂— |  C=O | 2 |  CF₃ | 1690 1740 | (DMSO + CDCl₃) (a) 3 to 4.5 ppm, m, 12H; 3.9 ppm, s, 4H; 4.5 ppm, s, 3H; 4.55 ppm, s, 2H; 6.7 to 7.9 ppm, m, 8H; 3H exchangeable 3H |
| 17 | 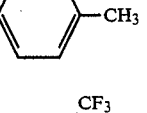 | —CH₂— | 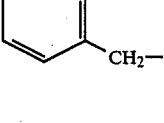 C=O | 3 |  Cl | 1680 1730 | (D₂O) (a) 1.6 to 2.2 ppm, m, 2H; 2.9 to 4.1 ppm, m, 16H; 4.2 ppm, s, 2H; 7 to 7.6 ppm, m, 4H; 7.8 to 8.9 ppm, m, 4H |
| 18 |  | —CH₂— | 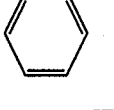 C=O | 3 | 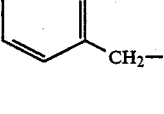 CH₃O | 1680 1730 | (D₂O) (a) 1.8 to 2.6 ppm, m, 2H; 3.3 to 4.3 ppm m, 16H; 3.9 ppm, s, 3H; 4.3 ppm, s, 2H; 7 to 8 ppm, m, 4H; 8 to 9 ppm, m, 4H |

-continued

COMPOUNDS OF GENERAL FORMULA I

| EX. | R₁ | A | B | n | R₂ | IR cm⁻¹ ν(C=O) | NMR (solvent) (b) = base (a) = acid |
|---|---|---|---|---|---|---|---|
| 19 | 2-pyridyl-CH₂- | -CH₂- | >C=O | 3 | 2-methylphenyl (o-CH₃) | 1680, 1730 | (DMSO—d₆) (a) 2.3 ppm, s, 5H; 2.8 to 4 ppm, m, 12H; 3.8 ppm, s, 4H; 4.3 ppm, s, 2H; 6.9 to 7.3 ppm, m, 4H; 7.7 to 9 ppm, m, 4H; exchangeable 3H |
| 20 | 2-pyridyl-CH₂- | -CH₂- | >C=O | 3 | 3-methylphenyl (m-CH₃) | 1680, 1730 | (DMSO—d₆) (a) 1.8 to 3 ppm, m, 5H; 3 to 4 ppm, m, 12H; 3.8 ppm, s, 4H; 4.35 ppm, s, 2H; 6.9 to 7.3 ppm, m, 4H; 7.5 to 9 ppm, m, 4H; exchangeable 3H |
| 21 | 2-pyridyl-CH₂- | -CH₂- | >C=O | 3 | 3-CF₃-phenyl | 1680, 1730 | (DMSO—d₆) (a) 1.5 to 2.1 ppm, m, 2H; 2.6 to 3.9 ppm, m, 12H; 3.8 ppm, s, 4H; 4.3 ppm, s, 2H; 6.9 to 7.9 ppm, m, 7H; 8.5 ppm, d, 1H; exchangeable 4H |
| 22 | 3-pyridyl-CH₂- | -CH₂- | >C=O | 3 | 3-chlorophenyl | 1695, 1750 | (DMSO—d₆) (a) 1.6 to 2.3 ppm, m, 2H; 2.7 to 4 ppm, m, 10H; 4 ppm, s, 4H; 4 to 4.5 ppm, m, 2H; 4.35 ppm, s, 2H; 6.6 to 9.2 ppm, m, 8H; exchangeable 3H |
| 23 | (C₆H₅)₂CH- | -CH₂- | >C=O | 3 | 2-methylphenyl (o-CH₃) | 1680, 1740 | (CDCl₃) (b) 1.6 to 1.95 ppm, m, 2H; 2.25 ppm, s, 3H; 2.3 to 3.1 ppm, m, 10H; 3.3 ppm, s, 4H; 3.8 ppm, t, 2H; 4.3 ppm, s, 1H; 6.9 to 7.6 ppm, m, 14H |
| 24 | (C₆H₅)₂CH- | -CH₂- | >C=O | 3 | 3-CF₃-phenyl | 1680, 1735 | (CDCl₃) (a) 1.5 to 2.3 ppm, m, 2.6 to 3.2 ppm, m, 10H; 3.3 ppm, s, 4H; 3.65 ppm, t, 2H; 4.3 ppm, s, 1H; 5 ppm, s, 2H; 6.7 7.7 ppm, m, 24H; exchangeable 4H |
| 25 | (4-Cl-C₆H₄)(C₆H₅)CH- | -CH₂- | >C=O | 3 | 4-fluorophenyl | 1675, 1735 | (CDCl₃) (b) 1.5 to 1.7 ppm, m, 2H; 2.2 to 2.5 ppm, m, 6H; 2.9 to 3.1 ppm, m, 4H; 3.2 ppm, s, 4H; 3.7 ppm, t, 2H; 4.2 ppm, s, 1H; 6.8 to 7.2 ppm, m, 13H |
| 26 | (4-Cl-C₆H₄)(C₆H₅)CH- | -CH₂- | >C=O | 3 | 3-CF₃-phenyl | 1680, 1735 | (CDCl₃) (b) 1.5 to 2.3 ppm, m, 2H; 2.3 to 2.7 ppm, m, 6H; 3 to 3.5 ppm, m, 4H; 3.8 ppm, s, 4H; 4 ppm, t, 2H; 4.4 ppm, s, 1H; 7 to 7.7 ppm, m, 13H |

-continued

COMPOUNDS OF GENERAL FORMULA I

| EX. | R₁ | A | B | n | R₂ | IR cm⁻¹ $\nu(C=O)$ | NMR (solvent) (b) = base (a) = acid |
|---|---|---|---|---|---|---|---|
| 27 |  | —CH₂— | C=O | 3 | 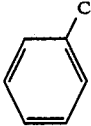CF₃ | 1690 1740 | (DMSO—d₆) (a) 1 to 2.4 ppm, m, 12H; 3 to 4.2 ppm, m, 13H; 4.35 ppm, s, 4H; 7 to 7.8 ppm, m, 4H; exchangeable 2H |
| 28 | 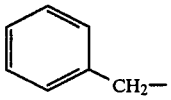 | C=O | —CH₂— | 3 | 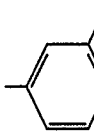CF₃ | 1700 1740 | (DMSO—d₆) (a) 1.5 to 2.1 ppm, m, 2H; 2.5 to 3.5 ppm, m, 16H; 4.8 ppm, s, 2H; 7 to 7.5 ppm, m, 9H; exchangeable 6H |
| 29 | 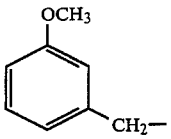 OCH₃ | C=O | —CH₂— | 3 | 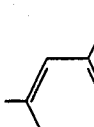CF₃ | 1695 1740 | (DMSO d₆ + CDCl₃) (a) 1.7 to 2.3 ppm, m, 2H; 2.3 to 4 ppm, m, 16H; 3.7 ppm, s, 3H; 4.8 ppm, s, 2H; 6.6 to 7.6, m, 8H; exchangeable 6H |
| 30 | 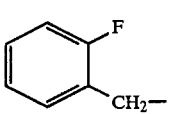F | —CH₂— | C=O | 3 | 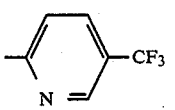CF₃ | 1730 1680 | (CDCL₃) (b) 1.7 to 2.2 ppm, m, 2H; 2.25 to 3.00 ppm, m, 6H; 3.50 ppm, s, 4H; 3.75 ppm, s, 2H; 3.50 to 4.10 ppm, m, 6H; 6.65 ppm, d, 1H; 6.65 to 7.75 ppm, m, 4H; 7.60 ppm, d, 1H; 8.40 ppm, s, 1H. |

PHARMACOLOGICAL STUDY

EXAMPLE 31

Assessment of the anxiolytic activity by the four-plates test

The anxiolytic activity of the compounds of the general formula I was investigated in mice according to the method of Aron Simon Larousse and Boissier described in Neuropharmacology (1971) 10 p. 459–469). After treatment of the animals by means of different doses of the compounds of the invention administered intraperitoneally or orally, the increase in the percentage of transitions during the exploration of the base of the test cage, in the presence of electric shocks, was assessed. The results of this study are shown in Tables II and III.

TABLE II

| EXAMPLE | DOSE i.p. (mg · kg⁻¹) | % INCREASE IN THE RESPONSES (TRANSITIONS) |
|---|---|---|
| 1 | 5 | 65 |
| 4 | 5 | 37 |
|   | 25 | 67 |
| 6 | 25 | 37 |
| 10 | 25 | 85 |
| 15 | 20 | 52 |
| 16 | 10 | 41 |
| 21 | 5 | 69 |
| 22 | 10 | 44 |
| 23 | 10 | 47 |
|   | 25 | 77 |
| 24 | 25 | 62 |
| 27 | 25 | 73 |
| 28 | 25 | 82 |
| 29 | 25 | 49 |
| 30 | 5 | 40 |

TABLE III

| EXAMPLE | DOSE p.o. (mg · kg⁻¹) | % INCREASE IN THE RESPONSES |
|---|---|---|
| 1 | 50 | 64 |
| 4 | 25 | 35 |
|   | 50 | 58 |
| 15 | 10 | 61 |
|   | 50 | 90 |
| 26 | 25 | 69 |

EXAMPLE 32

Assessment of the anxiolytic activity by the "staircase" test

The anxiolytic activity of the compounds of the invention was investigated in rats according to the method described by Thiebot, Soubrié and Boissier in J. Pharmacol. 1976, 7, (1), p. 87–102.

In this test, behavior involving rearing movements is associated with a state of distress of the animal. The number of steps climbed represents the normal exploratory behavior of the rat introduced into the enclosure. Normally, an efficacious anxiolytic compound should decrease, during the test which lasts 3 minutes, the number of rearing movements without modifying the number of steps climbed, or on the contrary should increase this latter parameter.

As demonstrated by the results shown in Table IV, the compounds of general formula I significantly decrease the number of rearing movements without thereby modifying the number of steps climbed.

TABLE IV

| EXAMPLE | DOSE i.p. (mg · kg⁻¹) | % VARIATION IN THE REARING MOVEMENTS | % VARIATION IN THE STEPS CLIMBED |
|---|---|---|---|
| 1 | 2,5 | −20 | NS |
|   | 10 | −39 | NS |
|   | 20 | −64 | NS |

TABLE IV-continued

| EXAMPLE | DOSE i.p. (mg·kg$^{-1}$) | % VARIATION IN THE REARING MOVEMENTS | % VARIATION IN THE STEPS CLIMBED |
|---|---|---|---|
| 4 | 10 | −47 | NS |
| 5 | 1,25 | −40 | NS |
| 15 | 10 | −43 | NS |
|  | 20 | −64 | NS |
| 20 | 2,5 | −43 | NS |
| 27 | 2,5 | −41 | NS |

NS: not significant

EXAMPLE 33

Assessment of the anxiolytic activity by MacMillan's conflict test

In these conditioning experiments which operate in the presence of a food reward, performed in rats according to the method described by MacMillan in Fed. Proceedings, 1975, 34, (9), p. 1870–1879, two parameters in the animal's behavioral responses are considered. The first parameter is the variation in the level of punished responses, in the presence of an electric shock, under the influence of the treatment in comparison with the level of punished responses under the influence of physiological saline. The second parameter is the variation in the level of unpunished responses, without an electric shock, under the influence of the same treatment, in comparison with the level of unpunished responses when physiological saline is administered. A specific anxiolytic effect is established when, after the administration of a substance, the level of only the punished responses is increased. The compounds of general formula I give positive results in this test, as shown in Table V.

TABLE V

| EXAMPLE | DOSE i.p. (mg·kg$^{-1}$) | % VARIATION IN THE PUNISHED RESPONSES | % VARIATION IN THE UNPUNISHED RESPONSES |
|---|---|---|---|
| 1 | 2,5 | +49 S | +18 NS |
| 10 | 5 | +67 S | +18 NS |
| 14 | 5 | +48 S | +14 NS |
| 15 | 10 | +41 S | +37 NS |

S = significant
NS = not significant

EXAMPLE 34

Assessment of the anxiolytic activity by the Geller-Seifter test

The anxiolytic activity of the compounds of the present invention was also assessed in rats with the Geller-Seifter test described by Geller, Kulac and Seifter in Psychopharmacologia, 1962, 3, p. 374–375.

As in the case of the previous test, the parameters of punished responses (with electric shock) and unpunished responses (without shock) are taken into account for demonstrating an anxiolytic effect on the part of the test substances. An increase related exclusively to the levels of the punished responses determines the existence of an authentic anxiolytic effect.

The compounds of the present invention significantly affect the level of punished responses. By way of example, the compound of Example 1 at a dose of 2.5 mg.kg$^{-1}$ (i.p.) and the compound of Example 2 at a dose of 5.0 mg.kg$^{-1}$ (i.p.) increase the punished responses by 39% ($p<0.05$) and 65% ($p<0.05$), respectively.

EXAMPLE 35

Inhibition of isolation-induced aggression in mice

The compounds of general formula I inhibit the attacking behavior of mice rendered aggressive by isolation according to the method described by Yen, Stanger and Millman in Arch. Int. Pharmacodyn. 1959, 123, p. 179–185. The effective dose (i.p.) inhibiting 50% of the aggressive animals (ED$_{50}$) is shown in Table VI.

TABLE VI

| EXAMPLE | Inhibitory ED$_{50}$ (mg·kg$^{-1}$, i.p.) |
|---|---|
| 1 | 7,64 |
| 6 | 4,74 |
| 9 | 8,60 |
| 17 | 6,11 |
| 19 | 6,78 |
| 21 | 11,08 |

EXAMPLE 36

Inhibition of aggression in isolated and bulbectomized rats

The compounds of the present invention inhibit aggression in isolated and bulbectomized rats. The inhibition of aggression was assessed according to the method described by Vergnes and Karli in C.R. Soc. Biol. 1963, 157, p. 1061. The effect on the aggression is assessed in terms of the percentage of animals which became non-killers after treatment. The results of this test are shown in Table VII.

TABLE VII

| EXAMPLE | DOSE i.p. (mg·kg$^{-1}$) | % OF NON-KILLER ANIMALS |
|---|---|---|
| 1 | 25 | 45 |
| 7 | 25 | 67 |
| 9 | 25 | 60 |
| 10 | 25 | 66 |
| 15 | 25 | 64 |
| 21 | 12,5 | 73 |
| 22 | 12,5 | 83 |

EXAMPLE 37

Inhibition of the active conditioned avoidance response in rats

The results obtained with the compounds of general formula I during the various experiments employing the method described by Courvoisier et al. in Arch. Int. Pharmacodyn., 1953, 92, p. 305–361 and by Janssen et al. in Arzneim, Forsch, 1965, 15, p. 104–117 are recorded in Table X. The values obtained for the percentage inhibition of the conditioned avoidance response (% ICAR) demonstrate that the compounds of the invention possess a useful possible antipsychotic property.

TABLE X

| EXAMPLE | DOSE i.p. (mg·kg$^{-1}$) | % ICAR |
|---|---|---|
| 7 | 10 | 30 |
|  | 15 | 48 |
|  | 20 | 79 |
| 18 | 10 | 18 |
|  | 15 | 35 |
|  |  | 56 |
| 19 | 20 | 26 |

TABLE X-continued

| EXAMPLE | DOSE i.p. (mg·kg$^{-1}$) | % ICAR |
|---|---|---|
| | 40 | 73 |

EXAMPLE 38
Investigation of side effects

The "rotating bar" test (bar driven at a speed of 4 revolutions per minute) performed in mice was used to investigate the muscle relaxant effect. The compounds of the invention, administered intraperitoneally 30 minutes before this test at a dose of 25 mg.kg$^{-1}$ and 50 mg.kg$^{-1}$, do not significantly increase the percentage of falls of the treated animals compared with the falls observed in the untreated controls.

The anticonvulsant effect of the compounds of the invention was investigated in mice by the electric shock test, as well as by testing for an antagonism towards pentylenetetrazole-induced convulsions.

The compounds of general formula I, administered intraperitoneally at a dose of 25 mg.kg$^{-1}$, do not protect the animals against the electric shock-induced convulsions. Likewise, the different compounds of the invention, at a dose of 50 mg.kg$^{-1}$, do not antagonize the convulsions induced by a dose of 100 mg.kg$^{-1}$ of pentylenetetrazole administered intraperitoneally.

PHARMACEUTICAL PREPARATION
EXAMPLE 39

Gelatin capsules containing a 2 mg dose of 4-(2-fluorobenzyl)-1-{3-[1-(3-trifluoromethylphenyl)-4-piperazinyl]propyl}-2,6-piperazinedione dimandelate

| | |
|---|---|
| 4-(Fluorobenzyl)-1-{3-[1-(3-trifluoromethyl-phenyl)-4-piperazinyl]propyl}-2,6-piperazinedione | 2 mg |
| Corn starch | 15 mg |
| Lactose | 25 mg |
| Talc | 5 mg |

We claim:
1. A compound of general formula I

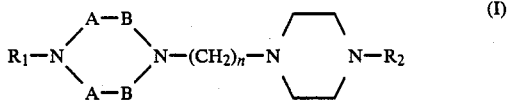

in which
 A and B each denote a methylene radical or a carbonyl radical with the proviso, however, that A and B never simultaneously denote the same radical,
 $R_1$ denotes a diphenylmethyl radical optionally substituted on the benzene rings with a halogen atom, a cyclohexyl radical, a pyridylmethyl group, or a benzyl radical optionally substituted with a halogen atom or with an alkoxy radical containing from 1 to 4 carbon atoms,
 $R_2$ denotes a pyrimidinyl radical or a phenyl radical optionally substituted with a halogen atom, with an alkyl radical having from 1 to 4 carbon atoms, with a trifluoromethyl radical or with an alkoxy radical containing from 1 to 4 carbon atoms,
 n is an integer which can assume values from 2 to 4, and their salts formed by addition to a pharmaceutically acceptable inorganic or organic acid.

2. Compound of claim 1 which is 4-(2-Fluorobenzyl)-1-{3-[1-(3-trifluoromethylphenyl)-4-piperazinyl]propyl}-2,6-piperazinedione and its addition salts with a pharmaceutically acceptable inorganic or organic acid.

3. Compound of claim 1 which is 4-(2-Methoxybenzyl)-1-{3-[1-(3-trifluoromethylphenyl)-4-piperazinyl]propyl}-2,6-piperazinedione and its addition salts with a pharmaceutically acceptable inorganic or organic acid.

4. Compound of claim 1 which is 4-(2-Pyridylmethyl)-1-{3-[1-(3-trifluoromethylphenyl)-4-piperazinyl]propyl}-2,6-piperazinedione and its addition salts with a pharmaceutically acceptable inorganic or organic acid.

5. Compound of claim 1 which is 4-Benzyl-1-{3-[1-(4-fluorophenyl)-4-piperazinyl]propyl}-2,6-piperazinedione and its addition salts with a pharmaceutically acceptable inorganic or organic acid.

6. Compound of claim 1 which is 4-(2-Methoxybenzyl)-1-{3-[1-(4-fluorophenyl)-4-piperazinyl]propyl}-2,6-piperazinedione and its addition salts with a pharmaceutically acceptable inorganic or organic acid.

7. Compound of claim 1 which is 4-(2-Methoxybenzyl)-1-{4-[1-(3-trifluoromethylphenyl)-4-piperazinyl]butyl}-2,6-piperazinedione and its addition salts with a pharmaceutically acceptable inorganic or organic acid.

8. Compound of claim 1 which is 4-(2-Pyridylmethyl)-1-{3-[1-(2-chlorophenyl)-4-piperazinyl]propyl}-2,6-piperazinedione and its addition salts with a pharmaceutically acceptable inorganic or organic acid.

9. Compound of claim 1 which is 4-(2-Pyridylmethyl)-1-{3-[1-(2-methylphenyl)-4-piperazinyl]propyl}-2,6-piperazinedione and its addition salts with a pharmaceutically acceptable inorganic or organic acid.

10. Compound of claim 1 which is 4-(2-Chlorobenzyl)-1-{3-[1-(3-trifluoromethylphenyl)-4-piperazinyl]propyl}-2,6-piperazinedione and its addition salts with a pharmaceutically acceptable inorganic or organic acid.

11. Compound of claim 1 which is 1-(3-Methoxybenzyl)-4-{3-[1-(3-trifluoromethylphenyl)-4-piperazinyl]propyl}-2,6-piperazinedione and its addition salts with a pharmaceutically acceptable inorganic or organic acid.

12. A pharmaceutical composition containing, as active principle, a compound as claimed in claim 1, in combination or mixed with a pharmaceutically acceptable, non-toxic inert excipient or vehicle.

13. A pharmaceutical composition as claimed in claim 12, containing the active principle at a dose of 0.1 to 100 mg.

14. A method of treating a subject in need of anxiolytic or antiaggression, medication, comprising the step of administering to the said subject an effective anxiolytic or antiaggression amount of a compound of claim 1, or a pharmaceutical composition containing the same together with a pharmaceutically-acceptable excipient or vehicle.

* * * * *

UNITED STATES PATENT AND TRADEMARK OFFICE
CERTIFICATE OF CORRECTION

PATENT NO. : 4,820,707
DATED : April 11, 1989
INVENTOR(S) : Gilbert Lavielle and Jean C. Poignant It is certified that error appears in the above-identified patent and that said Letters Patent is hereby corrected as shown below:

Col. 1, line 41; "cycohexyl" should read -- cyclohexyl --
Col. 5, line 26; "-1-β-8 1-(3-tri-" should read
 -- -1-β-[1-(3-tri- --
Col. 5, line 40; "-1-β-8" should read -- -1-β-[ --
Col. 5, line 46; "-1-β-8" should read -- -1-β-[ --
Col. 6, line 51; "iospropyl" should read -- isopropyl --
Col. 8, line 51; "-trilfuoromethylphenyl)-4-" should read
 -- -trifluoromethylphenyl)-4- --
Cols. 9 & 10, in the Table, under the last column heading,
 7th line; after "m," (first occurrence) insert -- 2H; --
Cols. 11 & 12, in the Table, under the last column heading, last
 line of that column; "9 ppm," should read -- 9.1 ppm, --
Cols. 13 & 14, in the Table, under the last column heading,
 27th line in that column; after "m," insert -- 2H; --
Col. 18, line 68, under TABLE X, under second column heading,
 6th line is empty and should be filled in with -- 20 --
Col. 20, line 57; delete the comma "," after "antiaggression"

Signed and Sealed this

Tenth Day of April, 1990

Attest:

HARRY F. MANBECK, JR.

*Attesting Officer*    *Commissioner of Patents and Trademarks*